US012611350B2

(12) United States Patent
Becker

(10) Patent No.: US 12,611,350 B2
(45) Date of Patent: Apr. 28, 2026

(54) NEONATAL CARE SYSTEM AND CONTROL METHOD

(71) Applicant: GE Precision Healthcare LLC, Wauwatosa, WI (US)

(72) Inventor: Karen P. Becker, Laurel, MD (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 1119 days.

(21) Appl. No.: 17/533,901

(22) Filed: Nov. 23, 2021

(65) Prior Publication Data

US 2023/0157915 A1     May 25, 2023

(51) Int. Cl.
*A61G 11/00*          (2006.01)
*G16H 40/63*          (2018.01)

(52) U.S. Cl.
CPC .......... *A61G 11/009* (2013.01); *A61G 11/002* (2013.01); *G16H 40/63* (2018.01)

(58) Field of Classification Search
None
See application file for complete search history.

(56) References Cited

U.S. PATENT DOCUMENTS

| | | |
|---|---|---|
| 4,032,740 A | 6/1977 | Mittelmann |
| 4,295,475 A | 10/1981 | Torzala |
| 4,588,383 A | 5/1986 | Parker et al. |
| 5,913,685 A | 6/1999 | Hutchins |
| 6,409,654 B1 | 6/2002 | McClain |
| 6,453,186 B1 | 9/2002 | Lovejoy et al. |
| 6,697,671 B1 | 2/2004 | Nova et al. |
| 6,893,390 B1 | 5/2005 | Mackin |
| 7,245,956 B2 | 7/2007 | Matthews et al. |

(Continued)

FOREIGN PATENT DOCUMENTS

WO      WO-2021186418 A1 *  9/2021

OTHER PUBLICATIONS

EP application 22206352.1 filed Nov. 9, 2022—extended Search Report issued Mar. 24, 2023; 7 pages.

(Continued)

*Primary Examiner* — Charles A Marmor, II
*Assistant Examiner* — Marc D. Honrath
(74) *Attorney, Agent, or Firm* — Andrus Intellectual Property Law, LLP

(57)          ABSTRACT

A neonatal care system includes an enclosure configured to provide a microenvironment for a neonate, one or more physiological sensors configured to sense a plurality of physiological parameters of the neonate, one or more microenvironmental sensors configured to sense a plurality of microenvironmental parameters within the enclosure, and at least one external environmental sensor configured to sense at least one external parameter outside the enclosure. A control system is configured to control the microenvironment based on a plurality of control settings, track at least one setting change to any of the control settings and in corresponding time of change, and store at least one event and a corresponding time for each event. A longitudinal log is generated including each of the physiological parameters, microenvironmental parameters, external parameter, setting change, and event with respect to time. A display is then generated and displayed based on the longitudinal log.

18 Claims, 7 Drawing Sheets

(56)                    References Cited

U.S. PATENT DOCUMENTS

| | | | |
|---|---|---|---|
| 8,002,701 | B2 | 8/2011 | John et al. |
| 8,185,191 | B1 | 5/2012 | Shapiro |
| 8,369,924 | B1 | 2/2013 | Chang |
| 8,660,630 | B2 | 2/2014 | Chang |
| 8,689,788 | B2 | 4/2014 | Rabi |
| 8,690,771 | B2 | 4/2014 | Wekell et al. |
| 8,727,980 | B2 | 5/2014 | Coelho |
| 9,220,443 | B2 | 12/2015 | Silver et al. |
| 9,289,166 | B2 | 3/2016 | Ito |
| D772,252 | S | 11/2016 | Myers et al. |
| 9,521,977 | B2 | 12/2016 | Silver |
| 9,554,958 | B2 | 1/2017 | Richards |
| 9,649,333 | B2 | 5/2017 | Rabi |
| 9,713,445 | B2 | 7/2017 | Freeman et al. |
| 9,861,545 | B2 | 1/2018 | Cipriano et al. |
| 9,872,807 | B2 | 1/2018 | Falk et al. |
| 9,931,042 | B2 | 4/2018 | Mahar |
| 10,110,859 | B2 | 10/2018 | Kaestle |
| 10,322,060 | B2 | 6/2019 | Fleischacker et al. |
| 10,413,476 | B2 | 9/2019 | Giarracco et al. |
| 10,596,054 | B2 | 3/2020 | Underwood et al. |
| 10,688,003 | B2 | 6/2020 | Underwood et al. |
| 11,141,104 | B2 | 10/2021 | Cetingul et al. |
| 2002/0124295 | A1 | 9/2002 | Fenwick et al. |
| 2002/0196141 | A1 | 12/2002 | Boone |
| 2004/0172222 | A1* | 9/2004 | Simpson ............... G08B 21/02 702/189 |
| 2005/0215845 | A1 | 9/2005 | Mahony et al. |
| 2007/0213600 | A1 | 9/2007 | John et al. |
| 2007/0276273 | A1 | 11/2007 | Watson, Jr. |
| 2008/0125821 | A1 | 5/2008 | Blomquist |
| 2010/0080431 | A1 | 4/2010 | Datema et al. |
| 2011/0190611 | A1 | 8/2011 | Rabi |
| 2011/0270100 | A1 | 11/2011 | Chang |
| 2012/0035675 | A1 | 2/2012 | Walker et al. |
| 2012/0157796 | A1 | 6/2012 | Ten Eyck |
| 2012/0232357 | A1 | 9/2012 | Coelho |
| 2012/0265040 | A1 | 10/2012 | Ito |
| 2012/0302910 | A1 | 11/2012 | Freeman |
| 2013/0085320 | A1 | 4/2013 | Vyasarao |
| 2013/0150655 | A1 | 6/2013 | Ten Eyck et al. |
| 2014/0000609 | A1 | 1/2014 | Steinhauer et al. |
| 2015/0105636 | A1 | 4/2015 | Hayman et al. |
| 2016/0112681 | A1 | 4/2016 | Kaestle |
| 2016/0135758 | A1 | 5/2016 | Sabota |
| 2016/0206504 | A1 | 7/2016 | Giarracco et al. |
| 2016/0302719 | A1 | 10/2016 | Ezeuka |
| 2017/0068791 | A1 | 3/2017 | Hermann et al. |
| 2017/0156608 | A1 | 6/2017 | Mahar |
| 2017/0266399 | A1 | 9/2017 | Campana et al. |
| 2017/0347960 | A1 | 12/2017 | Falk et al. |
| 2018/0040255 | A1 | 2/2018 | Freeman et al. |
| 2018/0078163 | A1 | 3/2018 | Welch |
| 2018/0168903 | A1* | 6/2018 | Underwood ............ H04L 67/12 |
| 2018/0235513 | A1* | 8/2018 | Meftah .................. G01N 1/405 |
| 2018/0360324 | A1 | 12/2018 | Lorraine et al. |
| 2018/0368762 | A1 | 12/2018 | Cetingul et al. |
| 2019/0290522 | A1 | 9/2019 | Underwood et al. |
| 2020/0281532 | A1 | 9/2020 | Davis |
| 2021/0174917 | A1* | 6/2021 | Timme .................. G16H 40/63 |

OTHER PUBLICATIONS

Dragerwerk AG & Co., "The Caleo Effect", Communications & Sales Marketing, 15.06-3, 2015.

Dragerwerk AG & Co., "Closer to the ideal", Communications & Sales Marketing, 15.06-2, 2015.

* cited by examiner

NEONATAL CARE SYSTEM AND CONTROL METHOD

BACKGROUND

The present disclosure generally relates to a neonatal care system, such as an incubator, neonate warmer or hybrid device. More specifically, the present disclosure relates to a microenvironment platform that includes a plurality of modules that communicate with each other to carry out all of the functions required by the neonatal care system.

Prematurely born neonates require specialized treatment and care due to their small size and still-developing organs and physiological systems. After being born, premature neonates are typically placed in devices that create a carefully controlled microenvironment around the patient. The neonatal care system operates to control environmental conditions of the microenvironment, such as oxygen concentration, temperature, humidity, air circulation, and light in such a manner as to promote the health and well-being of the neonate patient.

One type of neonatal care system is generally referred to as an incubator in which the patient is placed within a full enclosure and the temperature within the enclosure is carefully controlled with convective heating provided by a forced flow of heated air into the enclosure. Within the microenvironment, the oxygen concentration and humidity can also be accurately controlled.

Another type of neonatal care system is referred to as a radiant warmer. The radiant neonate warmer has an overhead canopy with heating elements that produce radiant heat directed downward onto the neonate patient to maintain a temperature-controlled microenvironment around the neonate patient. Radiant warmers typically have a partial enclosure, with partial walls around the sides of the infant platform and an overhead portion containing the heater.

Hybrid systems are another type of neonatal care system that incorporates both convective heating systems and radiant heating systems, and hybrid systems can often operate as either a radiant warmer or an incubator. Hybrid systems have a movable enclosure that can be fully closed to operate as an incubator and fully opened when operating as a warmer.

Neonatal care systems typically have multiple operational elements that must be accurately controlled to maintain the microenvironment at desired levels. Further, the neonatal care system includes one or more displays that provide information to the treating clinician. The neonatal care system can also have multiple input devices that allow the clinician to control parameters and physical conditions of the neonatal care system. Each of these systems is accurately controlled.

In some embodiments, the neonatal care system is configured to offer multiple control modes where different combinations of elements being controlled. For example, in an "air control mode" where air temperature of the microenvironment is controlled based on air temperature readings from a temperature sensor measuring air temperature within the microenvironment (such as mounted on an inside a wall of the enclosure) compared to a set air temperature. As another mode example, the system may also be configured to operate in a "baby control mode" where the where air temperature of the microenvironment is controlled based on a temperature measurement(s) of the neonate (such as a core temperature sensor and/or a peripheral temperature sensor adhered to the neonate's skin). Alternatively or additionally, the system may be configured to control heading of the microenvironment in a manual mode where heater output, such as of the radiant heater, is controlled to provide a set output, such as based on a heater power percentage set by a clinician. The user interface of the system may be configured to enable the clinician to select from multiple control modes, such as to select between the air control mode, the baby control mode, and the manual mode just described.

SUMMARY

This Summary is provided to introduce a selection of concepts that are further described below in the Detailed Description. This Summary is not intended to identify essential features of the claimed subject matter, nor is it intended to be used as an aid in limiting the scope of the claimed subject matter.

In one embodiment a neonatal care system includes an enclosure configured to provide a microenvironment for a neonate, one or more physiological sensors configured to sense a plurality of physiological parameters of the neonate, one or more microenvironmental sensors configured to sense a plurality of microenvironmental parameters within the enclosure, and at least one external environmental sensor configured to sense at least one external parameter outside the enclosure. A control system is configured to control the microenvironment based on a plurality of control settings and to track at least one setting change to any of the control settings and a corresponding time of change. The control system is further configured to store at least one event and a corresponding time for each event. A longitudinal log is generated including each of the physiological parameters, the microenvironmental parameters, the at least one external parameter, the at least one setting change, and the at least one event with respect to time. A display is then generated and displayed based on the longitudinal log.

A method of controlling a neonatal care system providing a microenvironment for a neonate includes sensing a plurality of physiological parameters of the neonate with at least one physiological sensor, sensing a plurality of microenvironmental parameters within an enclosure of the neonatal care system with at least one microenvironmental sensor, and sensing at least one parameter outside of the enclosure with at least one environmental sensor. The microenvironment is controlled based on a plurality of control settings and one or more of the physiological parameters, the microenvironmental parameters, and the at least one external parameter. Setting changes to any of the control settings are tracked along with a corresponding time of change and at least one event is stored along with a corresponding event time for each event. A trend is identified in each of the physiological parameters, the microenvironmental parameters, and the at least one external parameter. A correlation is determined between the trend in one of the physiological parameters, the microenvironmental parameters, and the at least one external parameter and at least one of: i) the trend in another of the physiological parameters, the microenvironmental parameters, and the at least one external parameter, ii) one or more of the at least one setting change, or iii) one or more of the at least one event. A display is then generated that visually indicates the correlation.

Various other features, objects and advantages of the invention will be made apparent from the following description taken together with the drawings.

BRIEF DESCRIPTION OF THE FIGURES

The drawings illustrate the best mode presently contemplated of carrying out the disclosure. In the drawings.

DETAILED DESCRIPTION

Figure 1:
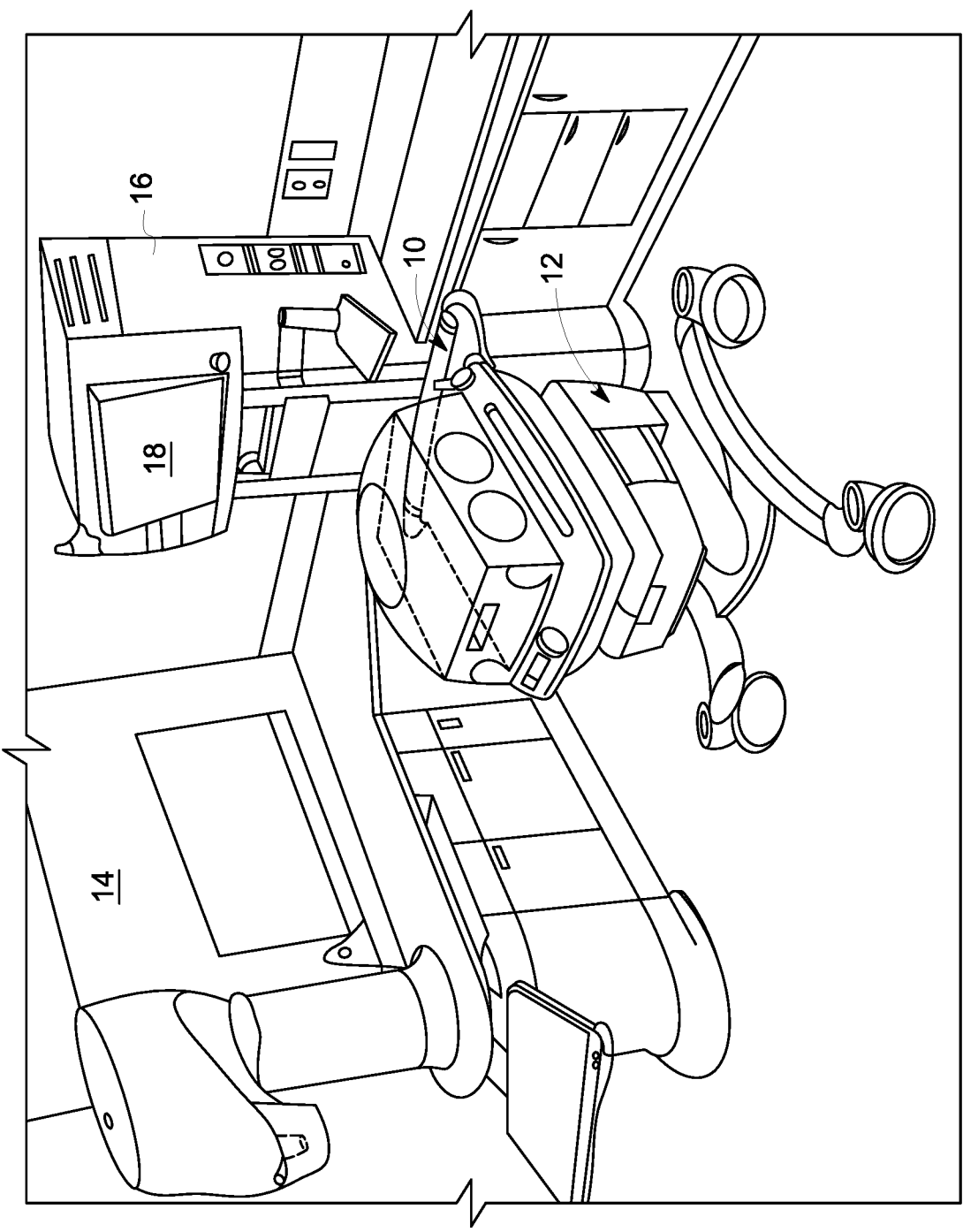
FIG. 1 is an environmental view that depicts an exemplary embodiment of a neonatal care system.

The present inventor has recognized problems with existing neonatal care systems that they do not enable or provide sufficient data or analysis to enable optimal thermal care for a neonate housed therein and/or to identify a source of a problem when a thermal issue occurs with the neonate. For example, when a neonate housed in a neonatal care system exhibits unstable temperature, typically clinicians may assume that the equipment—i.e., the neonatal care system— is the source of the problem. Thus, clinicians will troubleshoot the control settings for the neonatal care system and/or may check the function of the neonatal care system or may transfer the infant to a new neonatal care system if they suspect any malfunction. However, often the neonatal care system is not the source of the problem, the control settings are appropriate, and the system is functioning properly, but other factors have influenced the neonate's thermal condition and caused the instability. Other factors, such as external environmental factors in the environment of the neonatal care system and/or events, such as clinicians accessing the microenvironment to care for the neonate, changes in clothing or bedding, administration of medication, conducting procedures, etc., influence the neonate's thermal condition and causes instability. Similarly, setting changes to the neonatal care system and/or longitudinal trends in physiological parameters and/or parameters within the microenvironment may also provide information relevant to determining and diagnosing any thermal instability for the infant.

The neonatal care system and control method disclosed herein based on their recognition of the foregoing problems and challenges in the relevant art. The disclosed neonatal care system includes sensors configured to measure a plurality of parameters in and around the neonatal care system as well as psychological parameters of the neonate, and to track all system settings and events that occur with the system and/or the neonate and to generate a longitudinal log of all such data. The longitudinal log includes each physiological parameter, microenvironmental parameter, external parameter, setting change, and event with respect to time. Such information is then used to cross reference and correlate such information to provide early causal analysis of thermal issues occurring within the neonatal care system or with the neonate.

Changes in any of the measured physiological parameters, microenvironmental parameters, and/or external parameters monitored by the system may be compared across all information in the longitudinal log to assess correlation. Thereby, a correlation can be determined between the change in one of the physiological parameters, microenvironmental parameters, or external parameters and a change in another of the physiological parameters, microenvironmental parameters, or external parameters. Likewise, a correlation may be detected between the change in the one parameter and a setting change with the neonatal care system or the occurrence of an event, such as a care procedure performed by a clinician, a medication administration, changing a mattress or clothing on the neonate, opening the enclosure of the microenvironment, etc.

Such data analysis across multiple modalities and longitudinally over time enables early detection of thermal issues, such as by detecting changes in external or microenvironmental parameters prior to them affecting the neonate. Moreover, time-based analysis of the multiple modalities allows correlation and causal analysis of thermal changes that can lead to appropriate responses. For example, changes in a microenvironment parameter or a physiological parameter of the neonate caused by an event, such as a care procedure by a clinician, may necessitate a different response than a changed caused by an external parameter outside of the enclosure, and likewise will be responded to differently than a thermal change due to a setting change with the neonatal care system.

Accordingly, enabling and/or performance of causal association for thermal issues leads to better medical care for the neonate. The display may be controlled to visually indicate any correlation between various modalities. For example, portions of the displayed longitudinal log representing the correlation may be highlighted and/or any causal relationship between two modalities may be highlighted, such as by circling or otherwise organizing relevant portions of the displayed parameters and other modalities to visually indicate the causal relation. Alternatively or additionally, the display may include a textual explanation of the correlation, such as to call out or explain the causal relationship between the modalities.

The monitored parameters may include one or more of each of a physiological parameter, a microenvironmental parameter, and an external parameter. The system may be configured to monitor at least one physiological parameter, and in some embodiments a plurality of physiological parameters, including peripheral temperature of the neonate, a core temperature of the neonate, a temperature differential between the peripheral temperature and the core temperature, a weight of the neonate, and a heart rate of the neonate, among others. The system may be configured to monitor one or more microenvironmental parameters, and in some embodiments a plurality of microenvironmental parameters, including a measured air temperature, a measured humidity, a measured oxygen level, a tower consumption of the neonatal care system, and others. The system may further be configured to sense and track one or more external parameters, and in some embodiments a plurality of external parameters including a room temperature of an area surrounding the enclosure, a draft measurement of the area surrounding the enclosure, and a room humidity of the area surrounding the enclosure.

The system may be configured to track a setting change to any of the control settings for the neonatal care system, along with a corresponding time of the change. Setting changes may include, without limitation, a change in set temperature for controlling the care system, a change in set humidity for controlling the care system, a change in temperature control mode for the care system, and a change in set oxygen for the care system.

The system may further be configured to store one or more events along with an event time for each event. The events may include automatically detected events that are detected and logged automatically by the care system, and/or may include clinician-entered events that are inputted by a clinician for entry into the longitudinal log and inclusion in the correlation analysis conducted by the system. Automatically detected events may include, as non-limiting examples, an air boost action where one or more blowers within the microenvironment are activated to create an air curtain along a perimeter or other portion within the microenvironment, a temperature probe off event where a temperature probe is no longer properly adhered to the skin of a neonate, and enclosure open event where the enclosure of the microenvironment is open (such as lowering a side door of the enclosure or lifting the top cover or roof of the enclosure) and/or a port door opening where one or more smaller doors are opened through which a caregiver can reach in to access the neonate. In various embodiments, the care system may be configured to automatically detect some or all such actions, and/or to detect additional events that occur in or around the care system. For those events that can occur but the care system is not configured to automatically detect, the care may be configured to facilitate a clinician to enter such an event for documental in the longitudinal log. As non-limiting examples, the clinician entered event may include any one or more of a skin temperature probe fell off event, a skin temperature probe reposition event, a neonate reposition event, a medication administration, a phototherapy administration, a care procedure, a clothing change on the neonate, a blanket change on the neonate, a mattress change in the microenvironment, or the like. For example, a user interface of the care system may be configured such that a clinician can select from a list of common events and care actions and/or can otherwise enter an event, along with a corresponding event time.

In certain embodiments, the neonatal care system is configured to generate a display based on the longitudinal log which visually depicts various modalities and any correlation or causal relation therebetween. For example, in one embodiment the display based on the longitudinal log depicts a rolling time duration of each of the physiological parameters, the microenvironmental parameters, the external parameters, the setting changes, and the events, which are shown with respect to a common time axis.

FIG. 1 depicts an environmental view of a neonatal care system 10 in an environment, which in this example is a neonatal intensive care unit (NICU) 14 room. The neonatal care system 10 is depicted in this embodiment as an incubator; however, it will be recognized and understood from the disclosure and examples given herein that alternative embodiments of the neonatal care system 10 may include, but are not limited to, an incubator, a warmer and a hybrid warmer/incubator apparatus.

The neonatal care system 10 includes a mobile base 12 such that the neonatal care system 10 can be moved about a medical care facility, such as into the NICU 14. In the embodiment depicted in FIG. 1, the neonatal care system 10 is communicatively connected to a NICU workstation 16 that in embodiments provide additional functionality and data connections to the neonatal care system 10. The NICU workstation 16 can include a graphical display 18 that presents patient information to a clinician. As detailed herein, the graphical display 18 may be a touch-sensitive graphical display. In other embodiments, the graphical display 18 could be mounted to the neonatal care system 10.

Figure 2:
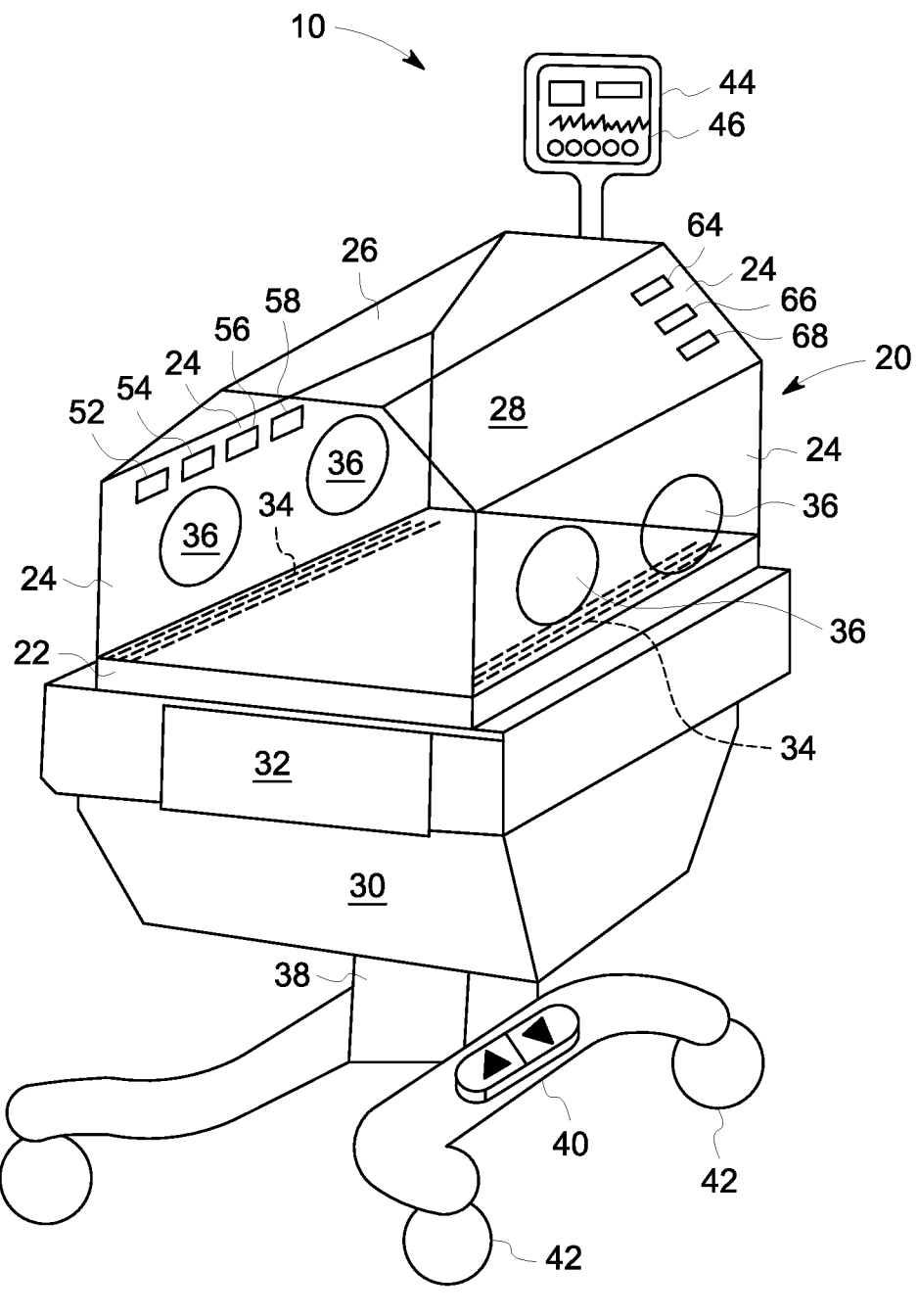
FIG. 2 exhibits another exemplary embodiment of a neonatal care system.

FIG. 2 depicts an exemplary embodiment of a neonatal care system in which the neonatal care system 10 is an incubator. The incubator has an enclosure 20 over a horizontal surface 22 that is configured to support a neonate patient (not depicted). It is to be understood that the horizontal surface 22 may have the ability or control to move, rotate, or incline.

One or more walls 24 extend generally vertically from the horizontal surface 22. In the embodiment depicted in FIG. 2 of the incubator enclosure 20, four walls extend vertically from the horizontal surface 22 to define the rectangular shape of the enclosure 20. However, it will be understood that in alternative embodiments, various numbers of walls 24 may be used to define the incubator into various geometric shapes which may include, but are not limited to, circles or hexagons. The enclosure 20 further includes a canopy 26 that extends over the horizontal surface 22. In some embodiments, as depicted in FIG. 2, the canopy 26 may include multiple components or surfaces, or as depicted in FIG. 1, the canopy may be curved or domed in shape.

While the incubator of FIG. 2 is depicted with the horizontal surface 22, walls 24, and canopy 26 being integrally connected, it will be understood that in alternative embodiments, including those described in greater detail herein, the horizontal surface 22, walls 24, and canopy 26 may be individual components that also may be moveable with respect to each other.

The horizontal surface 22, walls 24, and canopy 26 define a microenvironment 28 contained within these structures. The enclosure 20 is configured such that the microenvironment 28 surrounds the neonate patient (not depicted) such that the neonate patient is only exposed to a controlled combination of environmental conditions (temperature, humidity, $O_2$ concentration, etc.) selected by a clinician to promote the health and wellbeing of the neonate patient.

The enclosure 20 includes a base 30 that houses a convective heater 32. The convective heater 32 is operated such that air is drawn into the enclosure 20, at which point the air may be filtered or sterilized in another manner, including the use of UV light before being passed by heating coils (not depicted) to heat the air to a target or setpoint temperature. The sterilized and heated air is blown into the microenvironment 28 through vents 34 which are arranged along the walls 24. As is also known, the air may be entrained with supplemental gasses such as oxygen or may have added humidity such as to control these conditions within the microenvironment 28.

The walls 24 further include arm ports 36 that permit a clinician access into the microenvironment 28. While facilitating clinician access to the microenvironment 28, the arm ports 36, or the hands/arms of the clinician reaching into the microenvironment 28 through the arm ports 36, can be a source of introducing temperature change. As previously described, some embodiments of the enclosure 20 may align the vents 34 along the walls 24 in such a manner as to produce vertical jets of air along the walls 24 are operated in "air boost events" to help manage the microenvironment. These vertical jets of air generated during an air boost event create a barrier across the arm ports 36 which reduces the influx of outside air through the arm ports 36 from outside the microenvironment 28.

Embodiments of the enclosure 20 further include a pedestal 38 connected to the base 30. The pedestal 38 includes mechanical components (not depicted), which may include, but are not limited to, servo motors, rack and pinion systems, or screw gear mechanisms that are operable by foot pedals 40 to raise or lower the base 30, effectively raising or lowering the position of the neonate patient (not depicted) in relation to the clinician. As previously disclosed, the care system 10 may be moveable by wheels or casters 42 connected to the pedestal 38.

The exemplary embodiment of the care system 10 depicted in FIG. 2 includes a graphical display 44 that is mounted to a wall 24 or the canopy 26 of the enclosure 20 at a position external to the microenvironment 28. The graphical display 44 is operated by a processor to present a graphical user interface (GUI) 46. In the embodiment illustrated, the graphical display 44 is a touch-sensitive graphical display and the GUI 46 is configured to specifically respond to inputs made by a clinician received through the touch-sensitive graphical display. During normal operation, the touch-sensitive graphical display 44 and touch-sensitive configured GUI 46 are used to control various functions of the neonatal care system 10. The GUI 46 presents a variety of information, such as the air temperature and alarm indications.

Non-limiting examples of the alarms that may be presented at 50 can include, but are not limited to, threshold indications for physiological parameters such as cold stress, heat stress, tachycardia, bradicardia, excessive or insufficient respiration rate, excessive or insufficient temperature or disconnection of a physiological monitoring sensor. The GUI 46 further presents a variety of controls such as, but not limited to, control of the air boost, which in an embodiment refers to the aforementioned jets of air provided along the walls 24 by the vents 34.

Figure 3:
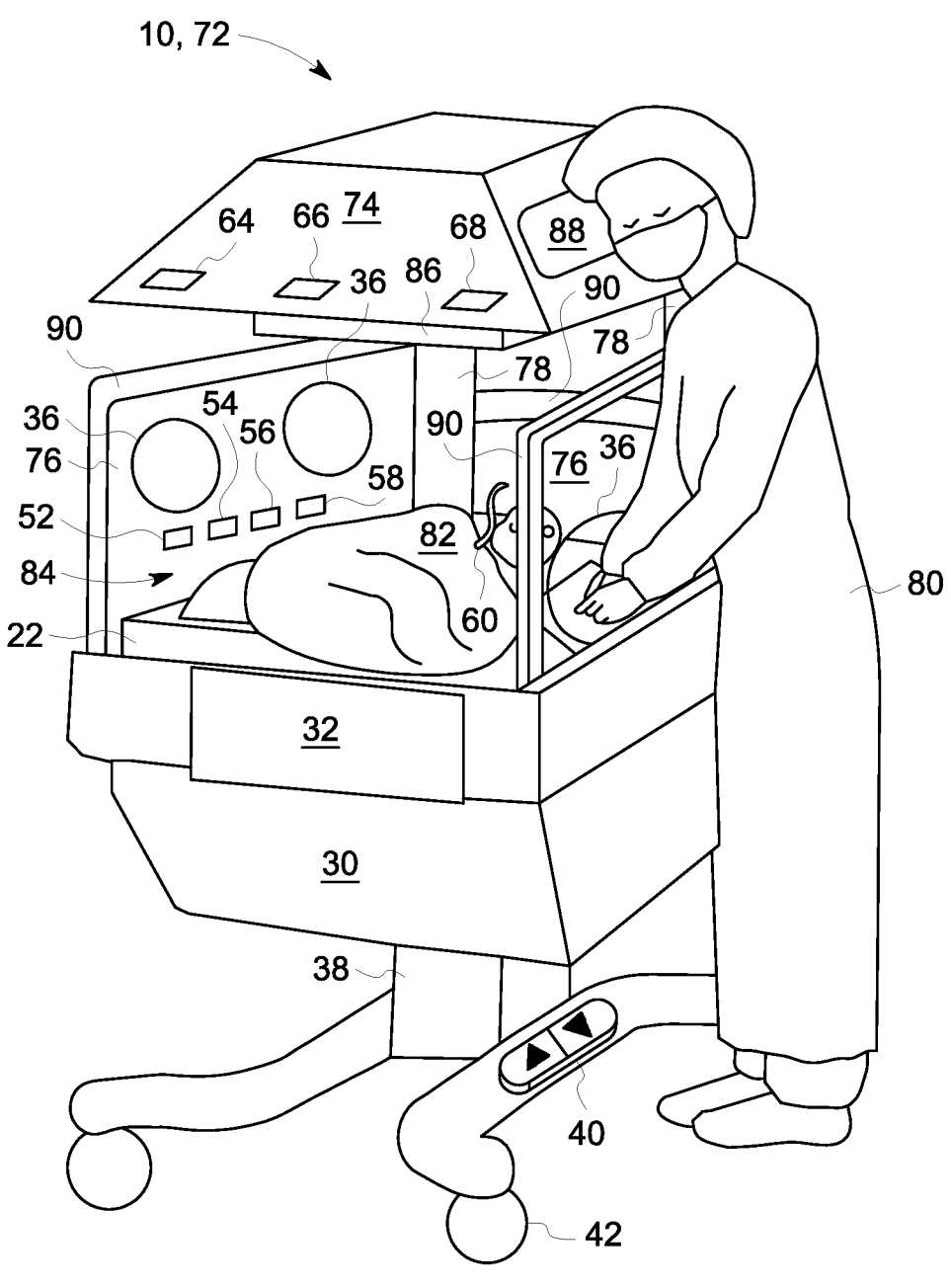
FIG. 3 depicts another exemplary embodiment of a neonatal care system.

FIG. 3 depicts an alternative embodiment of a neonatal care system in which the neonatal care system is a hybrid neonatal care system 72 that can functionally operate as either a warmer or an incubator. In a hybrid neonatal care system 72, the canopy 74 is separable from the walls 76. The canopy 74 is vertically moveable with respect to the walls 76 and the horizontal surface 22 on vertical rails 78. The walls 76 include one or more arm ports 36 through which the clinician 80 can access the neonate patient 82 located in the microenvironment 84 defined by the horizontal surface 22, walls 76, and canopy 74.

The hybrid neonatal care system 72 is operable between incubator and warmer modes. When the hybrid neonatal care system 72 operates as a radiant warmer, the canopy 74 may be vertically separated along the rail 78 along the horizontal surface 22, and a radiant heater 86 located in the canopy 74 produces radiant heat energy that is directed downward at the neonate patient 82, and thereby operates to control the temperature of the microenvironment around the neonate patient 82. When the hybrid neonatal care system 72 operates as an incubator, the canopy 74 is moved vertically closer to the horizontal surface 22 and the neonate patient 82 thereby enclosing or partially enclosing the neonate patient 82 in conjunction with the walls 76. In operation as an incubator, the hybrid neonatal care system 72 may control the temperature of the neonate patient 82 with a convective heater 32, while in other embodiments, the convective heater 32 and the radiant heater 86 may work in conjunction to effectively control the temperature of the neonate patient 82.

The embodiment of the hybrid neonatal care system 72 depicted in FIG. 3 includes a touch-sensitive graphical display 88 built into the canopy 74. The touch-sensitive graphical display 88 may operate in the manner as described above with respect to FIG. 2. It is also recognized that rather than being particularly located in the canopy 74, the touch-sensitive graphical display may alternatively be secured to the vertical canopy rails 78 or a wall rail 90. However, in these instances, the touch-sensitive graphical display 88 is located outside of the microenvironment 84.

As described above, the neonatal care system 10 includes a number of sensing devices, operational components and displays whose functions must be coordinated to allow the neonatal care system 10 to operate as desired. Embodiments of the neonatal care system 10, and as discussed in further detail herein, can control environmental conditions of the microenvironment in addition to temperature, including the oxygen concentration in the microenvironment 28, a humidity level within the microenvironment 28, lighting of the microenvironment, and/or noise and sound within the microenvironment 28. In such embodiments, the neonatal care system 10 can include a source of oxygen, exemplarily a cylinder of compressed oxygen gas, or a connection to a wall supply of oxygen in a medical care facility. Such oxygen from the oxygen supply can be applied to the microenvironment 28 through the convective heater 32. Furthermore, a humidifier (not depicted) can also provide humidity to the warmed medical gas (e.g., air or oxygen-enriched air) supplied to the microenvironment 28 by the convective heater 32. Furthermore, one or more light sources (not depicted) in the canopy 20 can control the light in the microenvironment 28.

The neonatal care system 10 includes a plurality of sensors that are configured to monitor various conditions within the microenvironment. In accordance with the above-disclosed environmental conditions of the microenvironment 28 that may be controlled by the neonatal care system 10, embodiments of the neonatal care system 10 may include microenvironmental sensors 50 such as an air temperature sensor 52, humidity sensor 54, oxygen sensor 56, light sensor 58, and/or a sound sensor (not depicted) configured to measure sound levels within the microenvironment. It is to be understood that the depicted temperature sensor 52, humidity sensor 54, oxygen sensor 56, and light sensor 58 may be located in various positions about the microenvironment 28, as would be recognized by one of ordinary skill in the art for these particular environmental conditions of the microenvironment 28. The sensed temperature, humidity, oxygen, and/or light from the respective sensors (52-58) are provided to the 10 (FIG. 4) of the neonatal care system 10 and used by the processor to control the environmental conditions maintained within the microenvironment 28 about the neonate patient 82.

The neonatal care system 10 further includes at least one physiological sensor 60 that is operable to obtain physiological data from the neonate patient 82. While a variety of physiological sensors may be used in various embodiments, as recognized by one of ordinary skill in the art, two non-limiting examples of such physiological sensors 60 includes a core temperature sensor configured to sense a skin temperature on the neonates core and a peripheral temperature sensor configured to sense a skin temperature on the neonate's extremity. Physiological sensors 60 may further include electrocardiographic sensors (ECG electrodes) to sense heart rate and/or rhythms, respiration sensors to sense respiration rate and/or waveforms, or a blood oxygenation (SpO2) sensor.

In embodiments, the temperature sensor 52, humidity sensor 54, oxygen sensor 56, light sensor 58, and physiological sensor 60 all operate in a continuous or generally continuous manner to monitor conditions of the microenvironment 28 and/or of the neonate patient 82. The continued or generally continuous measurements are provided to the aforementioned processor of the neonatal care system 10 and may be used by the processor to operate one or more of the convective heater 32, radiant heater 86, or other components of the neonatal care system. As described above, the neonatal care system may be configured to operate in various control modes based on the sensed parameters, such as air control mode, baby control mode, and manual mode described above.

Embodiments of the neonatal care system 10 may include one or more external environment sensors 63. These external environment sensors monitor the conditions outside of the neonatal care system 10, and more specifically, the environmental conditions outside of the microenvironment 28. External environment sensors 63 may exemplarily be one or more of an external temperature sensor 64, external humidity sensor 66, and draft sensor 68 such as a draft gauge configured to measure draft intensity. Other external sensors may be included, such as an external light sensor. While the external temperature sensor 64, external humidity sensor 66, and draft sensor 68 are depicted as being located on the canopy 20, it is to be recognized that in alternative embodiments, these sensors may be located in other positions on the neonatal care system outside of the microenvironment 28. The environmental data obtained from the external environment sensors is further provided to the control system 104 of the neonatal care system 10 such that the neonatal care system 10 uses this external environment data to further manage the microenvironment 28. Such management of the environmental conditions within the microenvironment 28, may control the operations of the convective heater or radiant warmer in response to a differential temperature between the microenvironment temperature and the temperature measured outside of the microenvironment. Further, these responses can be provided by the processor and to mitigate the detection of a draft about the neonatal care system 10.

Figure 4:
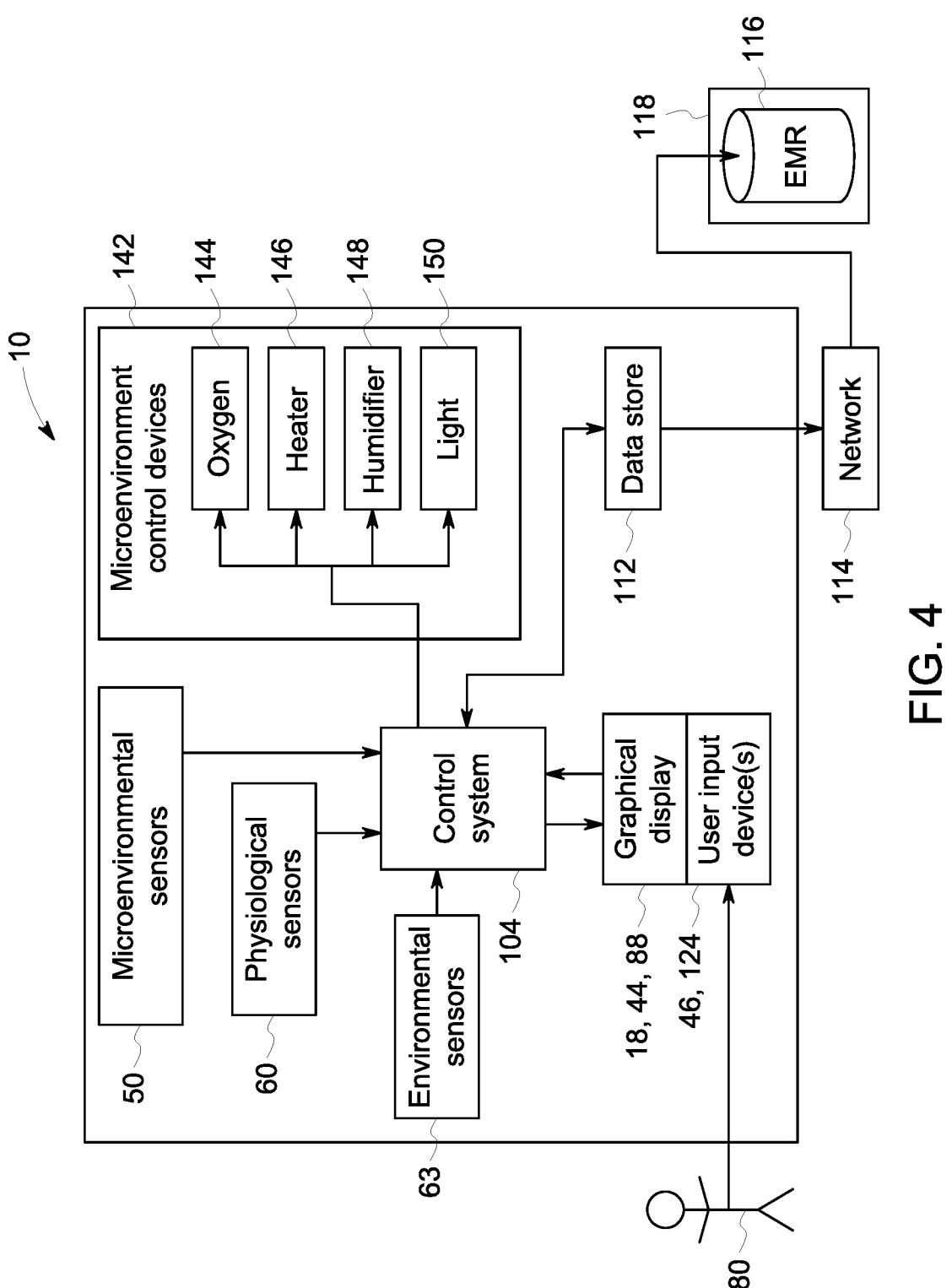
FIG. 4 is a system diagram of an exemplary neonatal care system.

FIG. 4 provides a schematic illustration of a neonatal care system 10 that coordinates the functions and activity. Control system 104 receives sensor information from the microenvironmental sensors 50, the physiological sensors 60, and the environmental sensors 63 and controls aspects of the care system 10 accordingly. The control system 104 includes one or more processors and a storage system configured to store software to be executed by the processor (s) such that the control system 104 carries out the functions and operations as disclosed herein. For example, the control system 104 may include a central processing unit (CPU) and may further include additional dedicated controllers for controlling various aspects of the system 10.

The control system 104 uses at least one analysis algorithm to process the physiological parameter data, the microenvironmental parameter data, and the external environmental parameter data. The processed data is provided to a data store 112, which is exemplarily volatile or nonvolatile computer memory that locally stores the processed data at the neonatal care system 10 for further use of the processed data at the neonatal care system 10 as described herein. The processed data at the data store 112 may exemplarily be physiological data, microenvironmental data, and/or external environmental data after basic processing such as digitization, filtering, and other signal processing or otherwise may be processed data that has been processed by more advanced algorithms such as to refine the saved physiological data, microenvironmental data, and/or external environmental data into specified values.

As described above, the neonatal care system 10 includes one or more microenvironment control devices 142 that are operated to control environmental conditions maintained within the microenvironment of the neonatal care system 10. The microenvironment control devices 142 exemplarily include an oxygen source 144, a heater 146, which may exemplarily be one or more of a convective heater and a radiant warmer, a humidifier 148, and/or a light source 150. The control system 104 operates the microenvironment control devices 142 which account for the additionally collected data, including detection of power consumption of the system 10 and/or the individual microenvironment control devices 142.

The control system 104 may further be configured to track and store any setting change for controlling the microenvironment 28 or any other aspect of the system 10. The tracked settings and setting changes, along with the corresponding time of each change, may be stored in the data store 112.

The control system 104 may further be configured to store one or more events and a corresponding event time for each in the data store 112. Stored events may be events detected by the control system 104, such as a change in position of the canopy 74, an enclosure open, a port door open, an air boost action, a temperature probe off event (or another physiological sensor off event). Such events may be detected by the control system 104 in various ways. For example, the canopy may be electromechanically controlled as described above, and a position sensor may be associated with the control system which provides a sensed canopy position to the control system 104. Enclosure open and/or port door open may be sensed using position sensors on elements of the enclosure, or it may be detected based on a sudden temperature decrease in a relevant portion of the microenvironment 28. The temperature probe off event may be determined based on an impedance measurement in the sensor, or otherwise based on a sudden change in the measured temperature indicative of the temperature probe no longer being properly adhered to the patient's skin. A similar process may be used for detecting loss of other physiological sensors 60 on the patient. Various other automatic event detections and methods for automatically detecting these and other events will be known to a person of ordinary skill in the art and are within the scope of the present disclosure.

Stored events may further include clinician-entered events entered by a clinician via a user interface element on or associated with the system 10, such as the GUI 46. The clinician-entered events entered by a clinician may relate to a care action or procedure, or an issue with the system 10 or the neonate addressed by the clinician. For example, the clinician-entered events may include a probe fell off event indicating that a temperature probe fell of the neonate and/or a probe reposition event indicating that the clinician moved and/or replaced the temperature probe. Such event information may supplement the auto-detected probe off event described above. Similar clinician entered events may be inputted regarding other physiological sensors. Events related to care actions on the neonate may include a neonate reposition event indicating that the neonate was moved by a clinician within the care system 10, a medication administration event indicating that medication was given to the neonate, a phototherapy administration event indicating that photo therapy was conducted (which may be over a period of time), a clothing change on the neonate (which may include and/or further specify adding or removing clothing and whether it was prewarmed), a blanket change on the neonate (which may include and/or further specify adding or removing a blanket and whether it was prewarmed), and a mattress change in the microenvironment, or other care procedure (such as feeding, cleaning, or otherwise attending to the neonate). A time or time period corresponding with each clinician entered event is also recorded, which may be a time entered by the clinician 80 or may be recorded as the time of the clinician input.

The clinician 80 may enter the event via the GUI 46 or other user input device 124, as well as enter other data and commands to the neonatal care system 10, which data and commands are provided back to the control system 104 and/or stored in the data store 112. The user input device 124 may include a touch screen, keyboard, buttons, dials, and/or other known devices for user interaction for controlling a care system 10 or information input to a computer system. The user input device 124 may be on or near the care system 10, such as the GUI 46 shown in FIG. 3, or may be separately located, such as elsewhere in the NICU 14 or at a central monitoring station.

In the depicted example, the data store 112 is further connected externally of the neonatal care system 10 to a data network 114. The data network 114 is exemplarily the network of the medical care facility within which the neonatal care system 10 is used. The data network 114 provides a communicative connection between the neonatal care system 10 and an electronic medical record (EMR) 116 of the neonate patient that may be stored on an EMR server 118 of the medical care facility. Thus, from the data store 112, the neonatal care system 10 can push the processed physiological and environmental data out to be recorded at the remotely stored EMR 116 of the neonate patient, while retaining some or all of the processed data locally at the data store 112 for later access and local use by the control system 104 and the neonatal care system 10.

The system 10 is configured to store the physiological parameter data, the microenvironmental parameter data, and the external environmental parameter data, along with the tracked setting changes and the stored events in a longitudinal log stored in data store 112. The longitudinal log relates each physiological parameter, microenvironmental parameter, external parameter, setting change, and event to a common time axis. Thereby, the longitudinal log provides the ability to compare and correlate the various data modalities with respect to one another and provides a means for analyzing the full extent of any thermal changes or trends and to locate causal links. For example, a causal link may be detected between an external environmental condition, such as an increased draft or decreased external temperature, and a change in physiological parameter data and/or microenvironmental parameter data. Likewise, a causal link may be detected between an event and a change in physiological parameter data and/or microenvironmental parameter data. Similarly, a causal link may be detected between a setting change and a change in physiological parameter data and/or microenvironmental parameter data.

The longitudinal log may comprise continuous parameter data or periodic parameter data. For example, the control system 104 may be configured to periodically store parameter data in the longitudinal log, such as to store a representative value every ten-minute period. In other embodiments the period may be shorter, such as five minutes, or longer, such as twenty minutes. The stored representative value may be an actual parameter data point, or may be a value calculated based on the parameter information in that period, such as a mean value, an average value, a filtered average value, etc.

Figure 5:
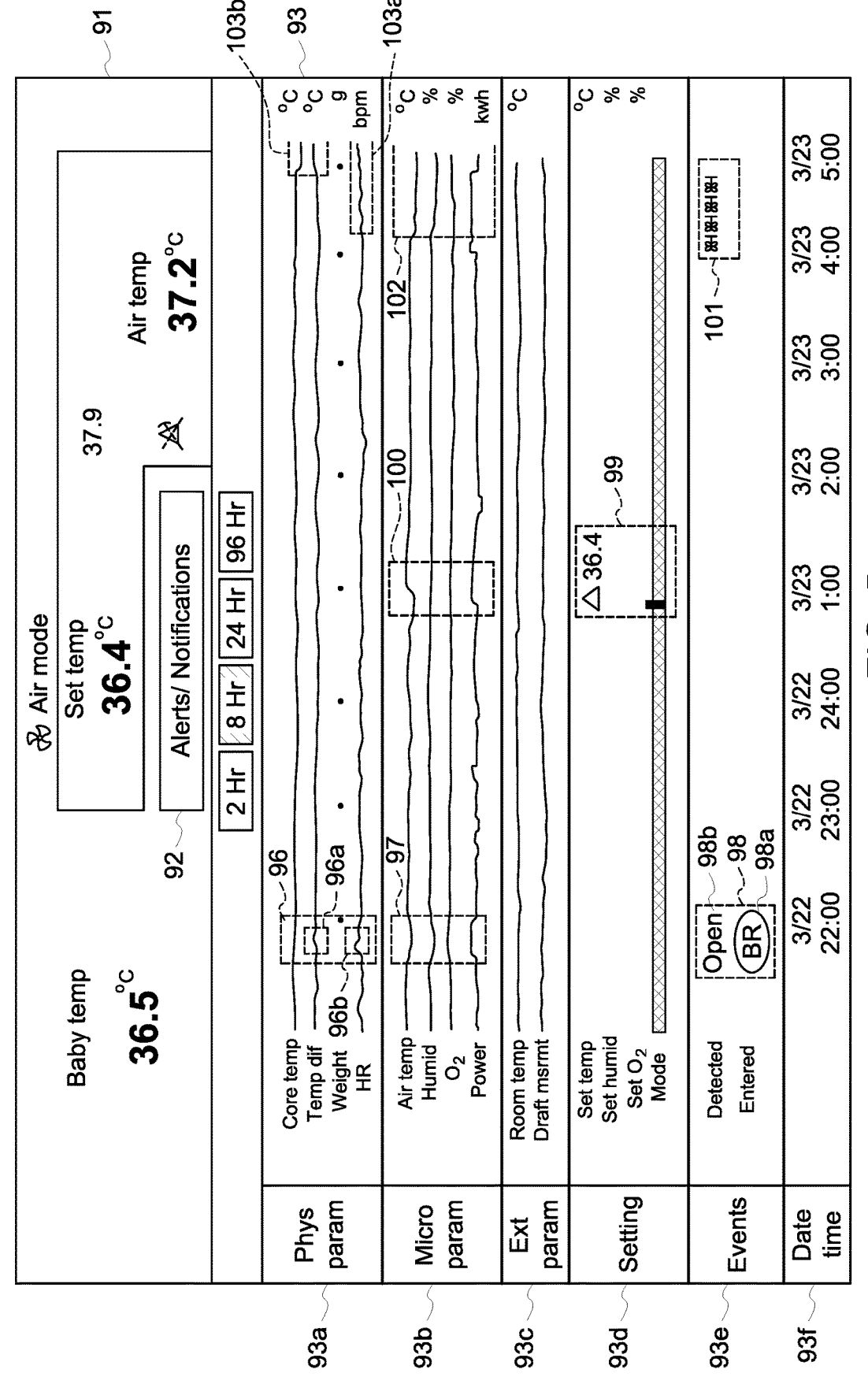
FIGS. 5-6 depict exemplary displays based on a longitudinal log in accordance with embodiments of the present disclosure.

The control system 104 may be configured to generate a display based on the longitudinal log. For example, the display may be configured to depict a rolling time duration of each of the physiological parameters, microenvironmental parameters, external parameters, setting changes, and events with respect to a common time axis. FIG. 5 exemplifies one such embodiment of a where a plurality of physiological parameters, microenvironmental parameters, external parameters, settings and setting changes, and events are presented with respect to a common time axis for a rolling time duration of 8 hours. Thus, as new data increments are added on the right side of the axis, data is shifted leftward, and the left-most data drops off the display 89. In the depicted example, the length of the rolling time duration is selectable by a clinician and the display 89 is adjusted accordingly, where 2-hour, 8-hour, 24 hour, and 96 hour rolling time durations of parameter data, settings, and events can be depicted.

On the top portion 91 of the display 89, various parameter measurements, mode settings, etc., are displayed. In the example, a baby temperature (such as a core temperature) is displayed along with a current measured air temperature within the microenvironment 28. The current set temperature and control mode are also displayed. The portion also includes an alert and notifications section 92 where any alert or notices are displayed, such as regarding changes in parameters and/or lace detected correlations. The alerts and notifications section 92 may also be configured to display alarms, such as threshold alarms and may be configured to provide correlations or further information about such alarms in addition to the alarm notification.

The display 89 further includes an exemplary longitudinal log display configured to depict selectable rolling time duration of each of the physiological parameters, the microenvironmental parameters, the external parameters, the setting changes, and the events with respect to a common time axis commensurate with the selected time duration. In the example, 8 hours of data from the longitudinal log are displayed. The longitudinal log display section 93 is configured with a physiological parameter display section 93$a$, a microenvironmental parameter display section 93$b$, an external parameter display section 93$c$, a settings display section 93$d$, and events display section 93$e$, and a date/time display section 93$f$. In the depicted example, the physiological parameters display section display a core temperature, a temperature differential between the core temperature and a peripheral temperature, a weight, and a heart rate. For each physiological parameter, 8 hours of information is displayed in the depicted example, core temperature, temperature differential, and heartrate are displayed as continuous lines rated by interrelating between discrete values. Weight is displayed as a discrete measurement value represented at an hourly interval. For example, a weight measurement may be conducted every hour and added to the longitudinal log. Alternatively, plurality of weight measurements may be conducted, such as over the hour, and a representative weight measurement may be calculated based on the plurality of weight measurements such as by determining an average or mean of the plurality of weight measurements. A person of ordinary skill in the art will understand in view of the present disclosure that each of the physiological parameters, and any parameter depicted herein may be displayed either as a continuous line or as a series of discrete measurement values. In other embodiments, alternative or additional physiological parameters may be included within the physiological section 93$a$. In some embodiments, the system 10 may be configurable by the clinician as to which parameters are displayed in each of the display sections 93$a$-93$f$.

The microenvironmental display section 93$b$ displays a plurality of microenvironmental parameters from the longitudinal log, including measured air temperature, measured humidity, measured oxygen, and power consumption of the neonatal care system. The external parameters section displays a plurality of external parameters from the longitudinal log, including measured room temperature of an area around the enclosure and a draft measurement of the area surrounding the enclosure. The setting display section 93*d* displays activity with respect to a plurality of settings for the system 10, including a set temperature, a set humidity, a set oxygen level, and a temperature control mode for controlling temperature within the microenvironment 28. The events section 93*e* depicts detected events and clinician entered events, which in the depicted embodiment are delineated to separate sections of the event section 93*e*. In other embodiments, events may be depicted in a single section. The date and time section 93*f* marks the time access for the rolling time period, and thus is adjusted according to the selected time duration for the display. In the depicted example, the date and time section 93*f* includes a date and time marker at hourly intervals. In other embodiments, higher or lower frequency of date and time markers may be included on the display which may be adjusted depending on the rolling time duration depicted in the longitudinal log display section 93.

The control system 104 may further be configured to identify a trend for each of the parameters, including each of the physiological parameter, the microenvironmental parameter, and the external parameter. The trend is based on a period of time of the parameter data and represents a change or lack of significant change in the data over that time. The trend may be based on the same time period length for each parameter, or trends for different parameters may be based on differing time period lengths depending on the qualities of that parameter. For example, the length of time of parameter data used for each trend may be based on the rate at which that parameter has a tendency to change so that the trend is configured to adequately represent the parameter. To provide one example, the trend for heartrate of the neonate may be based on a shorter time period length than the trend for core temperature of the neonate because heart rate tends to change much more quickly than core temperature. Likewise, a trend for patient weight may be based on a longer time duration of data since weight changes even more slowly and substantive changes in weight (or lack thereof) require analysis of a longer time period of a day or multiple days.

The control system 104 may further be configured to compare the parameter data trends to one another and to determine whether the trends correlate with one another. The correlation may be conducted via logic programs executed by the control system 104 regarding what types of trends, or value patterns over time, in various parameters correlate with trends or changes in other parameters. Likewise, logic may be executed correlating trends in various parameters with different types of events and different types of setting changes. Further logic may be included identifying certain setting changes or events as a causal source of certain parameter changes. Logic may also be included identifying certain parameter changes or trends as a causal source of other parameter changes or trends, particularly parameter changes or trends happening simultaneously or within a predetermined period of causally related parameter changes.

The display may be configured to depict how the trends in two or more different parameters or parameter types correlate with one another. FIG. 5 exemplifies depiction of correlations between parameter trends which facilitates determination of causal relations between the various trends and changes. When a changed trend is identified, such as in a physiological parameter, the system may be configured to correlate the change trend with change trends in other physiological parameters, any setting changes, and any events. In the example, change trends in physiological parameters are highlighted in box 96. In the example correlating change trends in the microenvironmental parameters are highlighted at box 97 and correlated events are highlighted at box 98. Thereby, the display visually indicates the correlation between the physiological parameters exhibiting a changing trend and changing trends in microenvironmental parameters and events that occurred. Specifically, changes in temperature differential are highlighted at box 96A and changes in heart rate occurring at approximately the same time are highlighted at box 96B. This draws the clinician's attention to the fact that the increase in temperature differential overlapped in time with the changes in heart rate. The display further visually indicates the changes in air temperature, humidity, and power consumption occurring during the same time period. Further, the display visually indicates that a baby reposition event 98A was entered by the clinician at the same time and an enclosure open event 98B was detected by the system at the same time. This visually indicates that the baby reposition event an opening of the enclosure is likely the cause of the change in the microenvironmental parameters and the physiological parameters for the baby, this indicates that the actions of the clinician are likely the cause of the change in parameters, rather than an issue with the neonatal care system or its settings, or an issue with the neonate, given that all parameters returned to a steady state after a period of time.

The setting section 93*d* of the display in the example is configured to depict setting changes of control settings for the neonatal care system 10. In the example, setting changes occur at about 1:00 AM, where a mode change from a baby mode to an air mode is marked as well as an increase in the set temperature. The changes are highlighted by box 99 in the display. Correlating change trends in the microenvironmental parameters are highlighted in box 100, which highlights an increase in air temperature and an increase in power consumption of the neonatal care system 10. In certain embodiments, the system may be configured to identify potential causal events, setting changes, or parameter trend changes in external parameters or microenvironmental parameters prior to the impact on the neonate's physiological parameters. In the example at FIG. 5, a series of air boost actions occur between 4:00 AM and 5:00 AM, several of which last for several minutes. The control system 104 is configured to identify events or series of events that are likely to impact the patients' physiological parameters, and particularly the patient's body temperature. The system is configured to detect a series of air boost events that occur within a threshold period of each other, such as a threshold number of air boost events within a half hour or within an hour. Air boost events typically occur when the microenvironment 28 is being accessed by a clinician such as through arm ports 36 or by lifting the hood or lowering a side wall 24. Opening the enclosure 20 has a tendency to cause a decrease in air temperature and humidity, and otherwise causes instability within the microenvironment 28. Thus, the control system 104 may be configured to identify when a threshold number of air boost actions have taken place and/or when air boost has been utilized for an extended period of time and to generate an alert of notification, or other visual indication on the display 89 alerting the clinician that excessive air boost events have occurred and may lead to instability within the microenvironmental parameters and/or the physiological parameters within the neonate. In the example, the excessive air boost events are highlighted in box 101. Later, the effects of the air boost events and accessing the microenvironment impacts the microenvironmental parameters, such as causing a threshold decrease in air temperature within the microenvironment and also a decrease in humidity. The change trends are detected by the controller as correlating the series of air boosts detected events, and the correlating trends across the microenvironmental parameters are highlighted at box 102. In various embodiments, each individual parameter may be highlighted, or a group of parameters may be highlighted together. A change trend in the heartrate is identified and correlated with the detected air boost event, which is highlighted in box 103A. Subsequently, a change occurs in the neonate's temperature, including a decrease in the neonate's core temperature and increase in the temperature difference. The temperature change trend is correlated with the trends in the microenvironmental parameters and also with the series of detected air boost events, and thus is highlighted in box 103B visually indicates the correlation.

Figure 6:
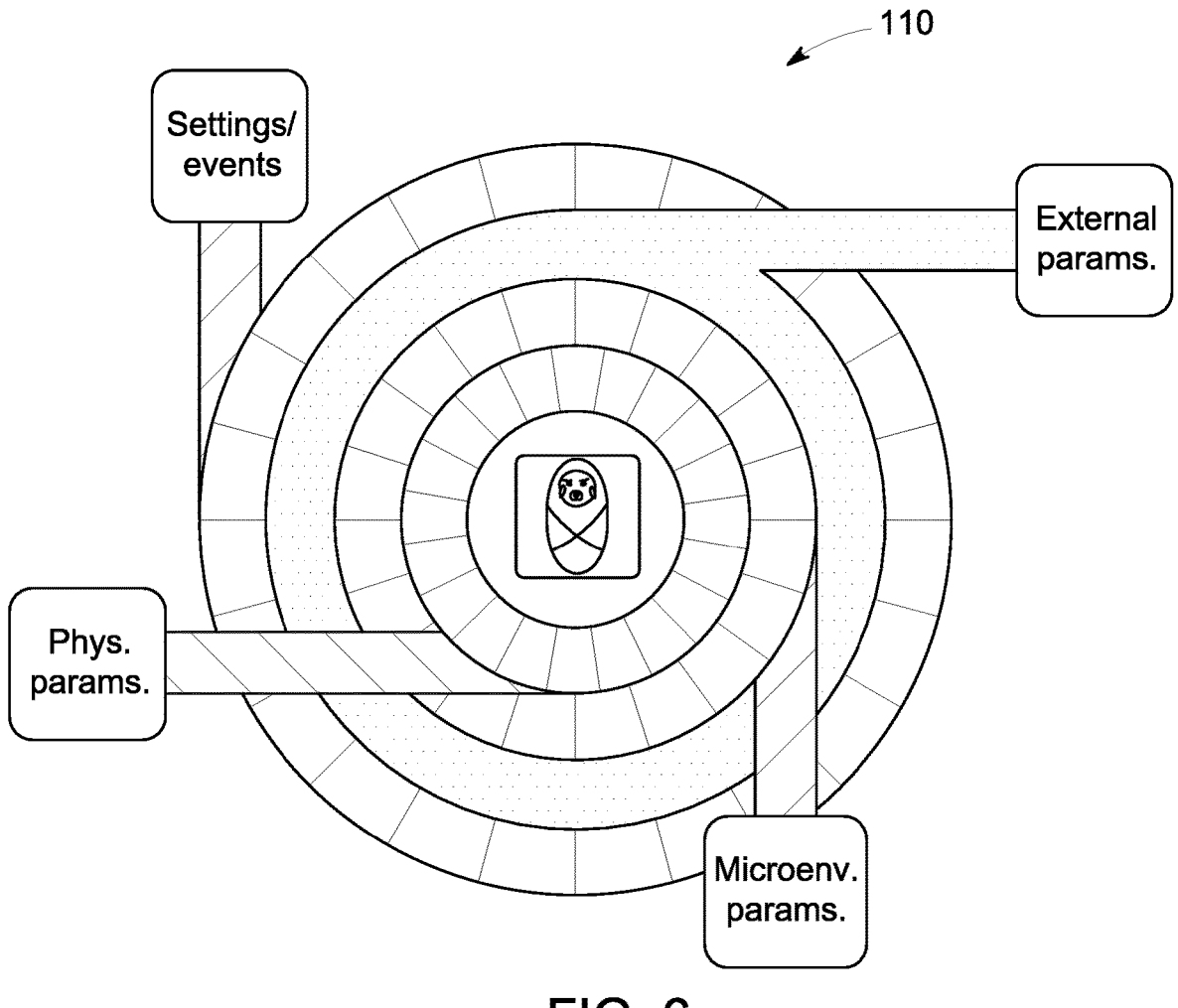

The display generated based on the longitudinal log visually communicates correlation between the various parameters, events, and settings, but may take various forms for such visual communication. FIG. 6 depicts another embodiment of a display 110 that may correlate with the 5 o'clock point in the example depicted in FIG. 5. In the display exemplified in FIG. 6, concentric circles are utilized to summarize each of the parameter types and the settings and events. The middle represents the neonate and may be configured to represent whether physiological parameters are stable and within ideal ranges, such as by a picture of a happy baby, or whether one or more of the parameters is outside of the threshold range or a trend exhibits a threshold change over a predetermined period of time, which may be represented by a picture of an upset baby as shown in the center of FIG. 6. Here, the temperature measurements of the neonate have exhibited a threshold change, and thus the crying baby image is pictured at the center.

The inner-most circle around the baby image represents the physiological parameters, such as those depicted in section 93*a* in FIG. 5. The next outer circle represents microenvironmental parameters, such as those depicted in section 93*b* of FIG. 5. The next outer circle represents external parameters, such as those represented in section 93*c* of FIG. 5. The most outer circle represents both settings and events, such as those represented in sections 93*d* and 93*e* in FIG. 5. If a correlation between a trend in one or the physiological parameters, the microenvironmental parameters and the external parameters correlates with a trend in another of the parameters or with a setting change or event, then the correlation is depicted by the highlighted relevant circle or ring. In the example at FIG. 6, each of the settings and events ring microenvironmental parameters ring and the physiological parameters ring are all highlighted indicating that a correlated change has occurred for at least one modality classified within that grouping. In other examples the diagram may include additional concentric rings. For example, each of settings changes and events may be represented separate concentric rings. In still other embodiments, parameters may have their own concentric ring, or each parameter may have its own concentric ring.

Figure 7:
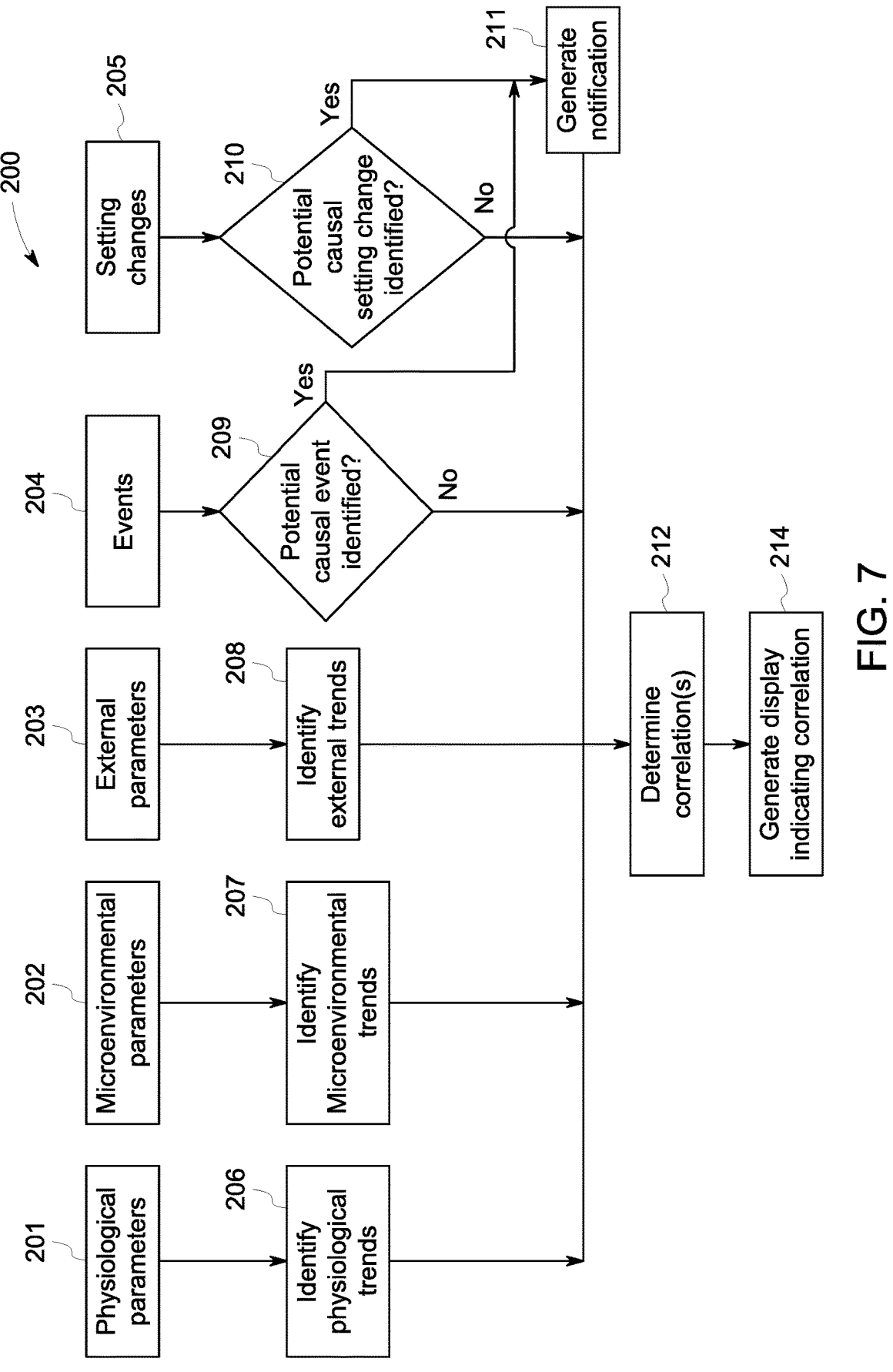
FIG. 7 depicts an embodiment of a method of controlling a neonatal care system in accordance with one embodiment of the present disclosure.

FIG. 7 is a flow chart depicted in one embodiment of the method of controlling a neonatal care system, or portion thereof. The method 200 includes receiving physiological parameters at step 201, microenvironmental parameters at step 202, external parameters at step 203, events at step 204, and setting changes at step 205. There are means and methods for collection of the parameter data, events, and setting change information are described herein. Trends are identified in each of the physiological parameters, the microenvironmental parameters and the external parameters. Physiological trends are identified at step 206 as trends in one or more of the physiological parameter data. Microenvironmental trends are identified at step 207 as trends in one or more of the microenvironmental parameters. External trends are identified at step 208 as trends in one or more of the external parameter data. Additionally, the event and setting change information is analyzed to identify potential causal events that may subsequently impact the future parameter data.

In the depicted embodiment, logic is executed at step 209 to determine whether the events at step 204 indicate a potential causal event which may impact one or more of the parameters. If so, then a notification of the potential causal event is generated at step 211, such as in the alerts and notifications section 92 the display 89 at FIG. 5. Alternatively or additionally, other visual indications of the potential causal events may be indicated, such as on the longitudinal display section 93 by highlighting the event or by highlighting the relevant ring in the embodiment at FIG. 6, to provide a few examples. Similarly, logic is executed at step 210 to determine whether a potential causal setting change can be identified that is likely to impact one or more of the parameters by a threshold amount, for example. If so, then a notification is generated at step 211. In other embodiments, the causal assessment may be skipped and the event and setting change information is only utilized for determining correlations. The trends, event information and setting change information are then analyzed at step 212 to determine whether any correlation exists between a trend or trends change in any one of the parameters compared to any of the other parameters, compared to the events, and/or compared to the setting changes. If a correlation is detected, then it is indicated on the display at step 214.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A neonatal care system comprising:

an enclosure configured to provide a microenvironment for a neonate;

one or more physiological sensors configured to sense a plurality of physiological parameters of the neonate;

one or more microenvironmental sensors configured to sense a plurality of microenvironmental parameters within the enclosure;

at least one external environmental sensor configured to sense at least one external parameter outside the enclosure;

a control system configured to:

control the microenvironment based on a plurality of control settings;

track at least one setting change to any of the control settings and a corresponding time of change;

detect at least one event, wherein the control system is configured to detect an air boost action, a temperature probe off, an enclosure open and/or a port door open, and at least one clinician-entered event;

store the at least one event and a corresponding event time for each event;

generate a longitudinal log representing each of the physiological parameters, the microenvironmental parameters, the at least one external parameter, the at least one setting change, and the at least one event with respect to time; and generate a display based on the longitudinal log.

2. The system of claim 1, wherein the display is configured to depict a rolling time duration of each of the physiological parameters, the microenvironmental parameters, the at least one external parameter, the at least one setting change, and the at least one event with respect to a common time axis.

3. The system of claim 1, wherein the control system is further configured to identify a trend in each of the physiological parameters, the microenvironmental parameters, and the at least one external parameter;

determine whether the trend in each of the physiological parameters, the microenvironmental parameters, and the at least one external parameter correlate with one another and to indicate the correlation.

4. The system of claim 3, wherein the display is configured to indicate the correlation between each of the physiological parameters, the microenvironmental parameters, the at least one external parameter, the at least one setting change, and/or the at least one event.

5. The system of claim 3, wherein the control system is further configured to determine whether the trend in each of the physiological parameters, the microenvironmental parameters, and the at least one external parameter correlates with one or more of the at least one setting change and to indicate the correlation.

6. The system of claim 3, wherein the control system is further configured to determine whether the trend in each of the physiological parameters, the microenvironmental parameters, and the at least one external parameter correlates with one or more of the at least one event and to indicate the correlation.

7. The system of claim 1, wherein the control system is configured to include a change in set temperature, a change in set humidity, a change in temperature control mode, and a change in set oxygen level as the at least one setting change tracked in the longitudinal log.

8. The system of claim 1, wherein user interface is configured to receive clinician input of the at least one clinician-entered event, wherein the control system is configured to include the at least one clinician-entered event in the longitudinal log.

9. The system of claim 8, wherein the at least one clinician-entered events includes one or more of a probe fell off, a probe reposition, a neonate reposition, a medication administration, a phototherapy administration, a clothing change on the neonate, a blanket change on the neonate, and a mattress change in the microenvironment.

10. The system of claim 1, wherein the plurality of physiological parameters includes at least three of a peripheral temperature of the neonate, a core temperature of the neonate, a temperature differential between the peripheral temperature and the core temperature, a weight of the neonate, and a heart rate of the neonate.

11. The system of claim 1, wherein the plurality of microenvironmental parameters includes at least two or more of a measured air temperature, a measured humidity, a measured oxygen level, and a power consumption of the neonatal care system.

12. The system of claim 1, wherein the one or more external parameters includes at least one of a room temperature of an area surrounding the enclosure, a draft measurement of the area surrounding the enclosure, a room humidity of the area surrounding the enclosure.

13. A method of controlling a neonatal care system providing a microenvironment for a neonate with a control system, wherein the neonatal care system comprises at least one of a heater, a humidifier, an oxygen source, and a light to control the microenvironment, and wherein the control system comprises one or more processors configured to receive and process sensor information from at least one microenvironmental sensor, at least one physiological sensor, and at least one environmental sensor, the method comprising:

sensing a plurality of physiological parameters of the neonate with the at least one physiological sensor;

sensing a plurality of microenvironmental parameters within an enclosure of the neonatal care system with the at least one microenvironmental sensor;

sensing at least one external parameter outside the enclosure with the at least one environmental sensor;

controlling the at least one of the heater, the humidifier, the oxygen source, and the light to control the microenvironment based on a plurality of control settings and one or more of the physiological parameters, the microenvironmental parameters, and the at least one external parameter;

tracking at least one setting change to any of the control settings and a corresponding time of change;

detecting at least one event, wherein the control system is configured to detect an air boost action, a temperature probe off, an enclosure open and/or a port door open, and at least one clinician-entered event;

storing the at least one event and a corresponding event time for each event;

identifying a trend in each of the physiological parameters, the microenvironmental parameters, and the at least one external parameter;

determining a correlation between one of the physiological parameters, the microenvironmental parameters, and the at least one external parameter and at least one of:

the trend in another of the physiological parameters, the microenvironmental parameters, and the at least one external parameter, one or more of the at least one setting change, or one or more of the at least one event; and generating a display that visually indicates the correlation.

14. The method of claim 13, further comprising:

generating a longitudinal log of each of the physiological parameters, the microenvironmental parameters, the at least one external parameter, the at least one setting change, and the at least one event with respect to time;

generating a display based on the longitudinal log;

wherein generating the display that visually indicates the correlation includes indicating the correlation on the display based on the longitudinal log.

15. The method of claim 14, wherein the display based on the longitudinal log depicts a rolling time duration of each of the physiological parameters, the microenvironmental parameters, the at least one external parameter, the at least one setting change, and the at least one event with respect to a common time axis, and wherein visually indicating the correlation includes highlighting a portion of the longitudinal log representing the correlation.

16. The method of claim 14, wherein tracking the at least one setting change includes storing a change in set temperature, a change in set humidity, a change in temperature control mode, and/or a change in set oxygen level as the at least one setting change tracked in the longitudinal log.

17. The method of claim 13, further comprising receiving clinician input of the at least one clinician-entered event, wherein the at least one clinician-entered event includes any one or more of a probe fell off, a probe reposition, a neonate reposition, a medication administration, a phototherapy administration, a clothing change on the neonate, a blanket change on the neonate, and mattress change in the microenvironment, wherein storing the at least one event includes storing the clinician-entered event.

18. The method of claim 13, wherein the plurality of physiological parameters includes at least three of a peripheral temperature of the neonate, a core temperature of the neonate, a temperature differential between the peripheral temperature and the core temperature, a weight of the neonate, and a heart rate of the neonate;

wherein the plurality of the microenvironmental parameters includes least two or more of a measured air temperature, a measured humidity, a measured oxygen level, and a power consumption of the neonatal care system; and wherein the at least one external parameter includes at least one of a room temperature of an area surrounding the enclosure, a draft measurement of the area surrounding the enclosure, a room humidity of the area surrounding the enclosure.

* * * * *